United States Patent [19]

Liautaud

[11] 4,015,600

[45] Apr. 5, 1977

[54] CATHETER NEEDLE ASSEMBLY

[76] Inventor: James P. Liautaud, River and Bluff Roads, Trout Valley, Cary, Ill. 60013

[22] Filed: July 7, 1975

[21] Appl. No.: 593,316

[52] U.S. Cl. .............................. 128/214 R; 16/150; 16/DIG. 13; 128/221

[51] Int. Cl.² ..................... A61M 5/00; A61M 5/32

[58] Field of Search ......... 128/214 R, 214.2, 214.4, 128/221, DIG. 16; 16/DIG. 13, 150; 403/291; 220/339

[56] References Cited

UNITED STATES PATENTS 3,064,648   11/1962   Bujan .............................. 128/214 R
3,720,979   3/1973   Krawagna ............................. 16/150

Primary Examiner—Dalton L. Truluck

[57]. ABSTRACT

A catheter needle assembly includes an injection-molded plastic body having a central hub portion through which a hollow core cannula extends, and from which a pair of wing-like tab portions extend in opposite directions to facilitate manipulating the assembly during use. Passageways extending through the roots of the tabs form crease lines to facilitate bending the tabs together for more convenient handling of the assembly.

1 Claim, 4 Drawing Figures

CATHETER NEEDLE ASSEMBLY

BACKGROUND OF THE INVENTION

The present invention is directed generally to catheter needle assemblies, and more particularly to a catheter needle assembly having an improved injection-molded body.

Catheter needles are widely used in hospitals and clinics for the injection of fluids into the human body. Typically, these needles include a hollow core needle or cannula which is inserted into a body cavity, and a body or handle attached to the cannula to facilitate positioning and insertion of the cannula. Principal considerations in the design and manufacture of such catheter needle assemblies are that they be compact in size, economical to manufacture, and present a minimal potential for contamination.

Catheter needle assemblies of the butterfly type, which include a thin plastic body having a central hub portion through which the cannula passes and from which a pair of wing-like handles or tab portions extend in diametrically opposed direction, have come into wide use because of their ease of storage and economy of manufacture. To enable the wing-like tab portions to be folded together to form a surface which can be conveniently grasped between the thumb and index finger, each of the tab portions of such assemblies has heretofore been provided with an axially extending channel or recess on the surface of its root, i.e. where the tab joins the central hub portion of the body. Unfortunately, such surface recesses increase the possibility of bacteria or other contaminants being retained on the surface of the catheter assembly and are therefore undesirable if a minimal potential for contamination is to be realized. Accordingly, the need has developed for a catheter needle assembly which does not have exposed channels or recesses on its exterior tab surface.

It is therefore a general object of the present invention to provide a new and improved catheter needle assembly.

It is another object of the present invention to provide a new and improved catheter needle assembly which has less potential for retaining contaminants.

It is another object of the present invention to provide a new and improved catheter needle assembly which has a smooth external surface free of channels or other contamination retaining recesses.

SUMMARY OF THE INVENTION

The invention is directed, in a catheter needle assembly of the type having an injection-molded body including a central hub portion and a pair of diametrically opposed wing-like tab portions extending in opposing directions from the hub portion, and a hollow core cannula centrally disposed through the hub portion, to the improvement comprising means including a pair of passageways extending through the body near the roots of respective ones of the wing portions in parallel spaced-apart relationship to the cannula for establishing a crease line at the roots of the tab portions whereby the tab portions fold about the crease lines to establish a surface for gripping the catheter needle assembly.

BRIEF DESCRIPTION OF THE DRAWINGS

The features of the present invention, which are believed to be novel, are set forth with particularity in the appended claims. The invention, together with the further objects and advantages thereof, may best be understood by reference to the following description taken in connection with the accompanying drawings, in the several figures of which like reference numerals identify like elements, and in which:

DESCRIPTION OF THE PREFERRED EMBODIMENT

Figure 1:
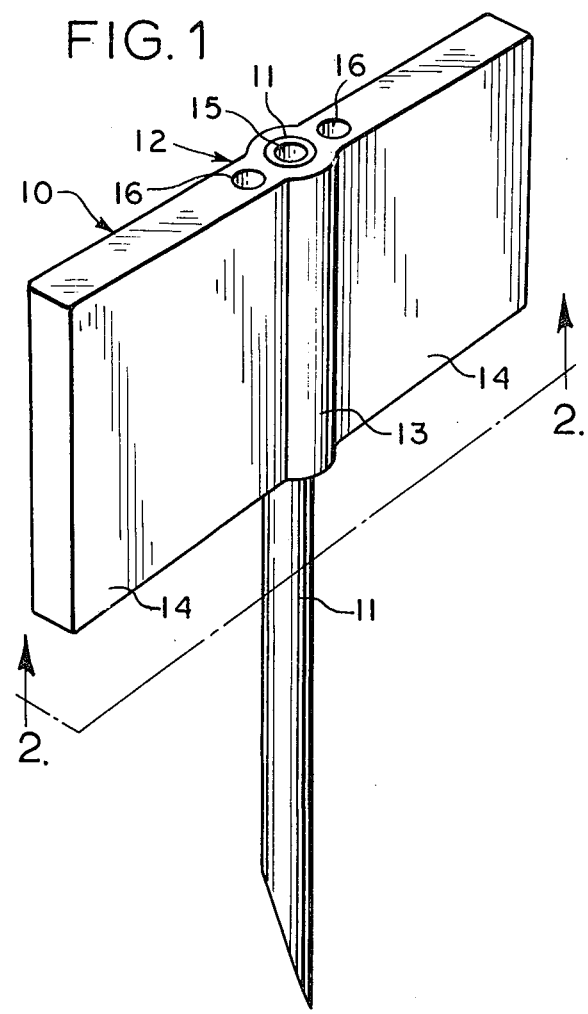
FIG. 1 is an enlarged perspective view of a catheter needle assembly constructed in accordance with the invention.

Referring now to the figures, and particularly to FIG. 1, a catheter needle assembly 10 constructed in accordance with the invention is seen to include a hollow core needle or cannula 11 having a pointed end for insertion into a body cavity and a blunt end for attachment to a tube extending from a source of fluid to be injected into the cavity. The blunt end of the cannula is embedded in an injection-molded body 12, which may be formed of a plastic by conventional injection-molding techniques. The body 12 is generally thin and cylindrical in form, having a central hub portion 13 of slightly increased thickness through which the cannula extends, and a pair of thin wing-like tab portions 14 extending from the hub portion in diametrically opposed directions. The hub portion is preferably cylindrical in form and axially aligned with the cannula 11, which is embedded therein such that its blunt end is flush with the top edge of the hub portion. The cannula, which includes a central passageway 15, may be formed of a suitable metallic material such as steel or stainless steel.

Figure 2:
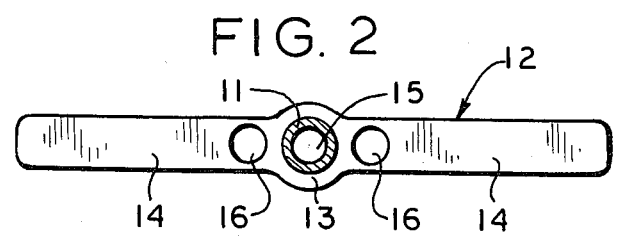
FIG. 2 is a cross-sectional view taken along line 2—2 of FIG. 1 showing the catheter needle assembly during storage and prior to being prepared for use.
Figure 3:
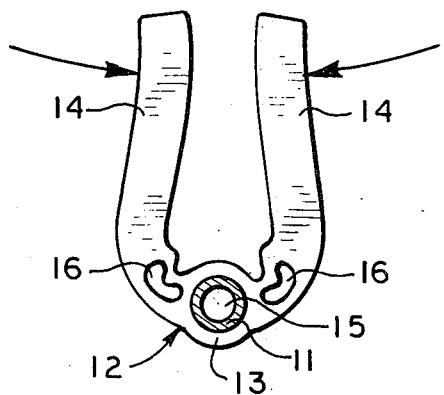
FIG. 3 is a cross-sectional view similar to FIG. 2 showing the catheter needle assembly with the tab portions of its body in a folded position in preparation for use.

In storage the catheter needle assembly 10 is packaged with the wing-like tabs 14 extending out in diametrically opposed directions as shown in FIG. 2. To facilitate guiding the cannula 11 into the body cavity, these tabs 14 are folded together as shown in FIG. 3 to provide a surface which can be grasped between the user's thumb and index finger. In accordance with the invention, to facilitate the bending of the tabs about their roots, i.e. about the point where they join the hub portion 13, with a desired degree of acuity, a pair of elongated apertures or passageways 16 are provided through the root portions of the tabs in a direction parallel to the spaced-apart from the axis of the cannula 11. The effect of these passageways is to form a crease line at the roots of the tabs about which the tabs bend as they are folded together prior to use of the catheter needle assembly, the reduced amount of material at the roots as a result of the passageways serving to reduce the force required to bend the tabs along the crease lines. Absent this provision the tabs would bow outwardly when bent and would not provide a surface which could be easily grasped.

Figure 1A:
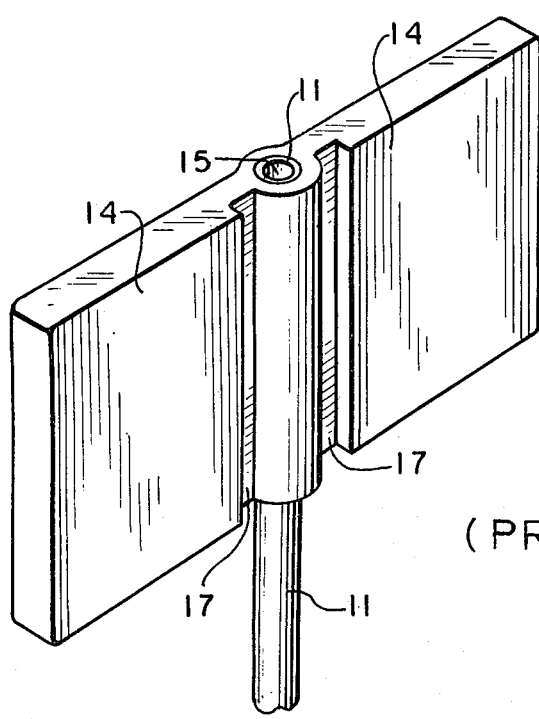
FIG. 1A is an enlarged perspective view similar to FIG. 1 showing a prior art catheter needle assembly.

Referring to FIG. 1A, in one prior art catheter needle assembly an acute bend was obtained at the roots of the tabs by the provision of channels 17 on the surface of the tabs. This had the disadvantage of providing recesses on the tab surface of the catheter needle assembly body within which bacteria or other contaminants could collect. Furthermore, the resulting assembly was not symmetrical, necessitating that the operator observe the position of the channels prior to bending the tabs.

In contrast, the passageways provided by applicant through the root portions of the tabs provide no such exposed recesses on the tab surfaces in which contamination can be collected, and provide a completely symmetrical assembly which can be manipulated in either direction without having to first determine the orientation or position of crease like forming channels.

While a particular embodiment of the invention has been shown and described, it will be obvious to those skilled in the art that changes and modifications can be made without departing from the invention in its broader aspect, and, therefore, the aim in the appended claims is to cover all such changes and modifications as fall within the true spirit and scope of the invention.

I claim:
1. In a catheter needle assembly of the type having
    a molded body including a central hub portion and a pair of diametrically opposed wing-like tab portions extending in opposite directions from a central axis, and
    a hollow-core needle embedded in and extending through said hub portion along said axis,
    the improvement comprising:
    means including a pair of passageways extending through respective ones of said tab portions adjacent said central hub portion in parallel spaced-apart relationship to said axis for establishing hinge lines between said tab portions and said hub portion to enable said tab portions to fold about said hub portion to provide a surface for gripping said catheter needle assembly.

* * * * *